United States Patent
Kim et al.

(10) Patent No.: US 10,718,027 B2
(45) Date of Patent: Jul. 21, 2020

(54) DETECTION METHOD FOR DNA REPAIR-RELATED GENES WHICH RESPOND TO LOW-LEVEL RADIATION

(71) Applicant: KOREA HYDRO & NUCLEAR POWER CO., LTD., Gyeongju-si, Gyeongsangbuk-do (KR)

(72) Inventors: Hee Sun Kim, Uijeongbu-si (KR); Dong Kwon Keum, Daejeon (KR); Hoon Choi, Seoul (KR); Kwang Hee Yang, Seoul (KR); Hyun Soon Bang, Uijeongbu-si (KR)

(73) Assignee: Korea Hydro & Nuclear Power Co., Ltd., Gyeongju-si, Gyeongsangbuk-do (KR)

( * ) Notice: Subject to any disclaimer, the term of this patent is extended or adjusted under 35 U.S.C. 154(b) by 0 days.

(21) Appl. No.: 15/521,282

(22) PCT Filed: Dec. 4, 2014

(86) PCT No.: PCT/KR2014/011853
§ 371 (c)(1),
(2) Date: Apr. 22, 2017

(87) PCT Pub. No.: WO2016/064023
PCT Pub. Date: Apr. 28, 2016

(65) Prior Publication Data
US 2019/0119754 A1   Apr. 25, 2019

(30) Foreign Application Priority Data
Oct. 22, 2014 (KR) .................. 10-2014-0143216

(51) Int. Cl.
| *C12Q 1/68* | (2018.01) |
| *C12Q 1/6886* | (2018.01) |
| *C12Q 1/686* | (2018.01) |
| *C12Q 1/6883* | (2018.01) |

(52) U.S. Cl.
CPC .......... *C12Q 1/6886* (2013.01); *C12Q 1/686* (2013.01); *C12Q 1/6883* (2013.01); *C12Q 2600/142* (2013.01); *C12Q 2600/158* (2013.01)

(58) Field of Classification Search
CPC ............... C12Q 1/6886; C12Q 1/6883; C12Q 2523/313; C12Q 2600/158
See application file for complete search history.

(56) References Cited

FOREIGN PATENT DOCUMENTS

| EP | 1 647 278 A1 | 4/2006 |
| KR | 10-2013-0086688 A | 8/2013 |
| KR | 10-2013-0125928 A | 11/2013 |
| KR | 10-2013-0125938 A | 11/2013 |
| KR | 20130125928 A | * 11/2013 | ........... C12Q 1/6883 |

OTHER PUBLICATIONS

Bong, JJ et al. Differential expression of thymic DNA repair genes in low-does-rate irradiated AKR/J mice. Journal of Veternary Science, vol. 14(3), p. 271-279, 2013.*
Schulaer, E et al. Effect of internal low-dose irradiation from 131 I on gene expression from normal tisusses from Balb/c mice. EJNMMI Research, vol. 1:29, p. 1-14. 2011.*
Skobowiat, C. et al. Cutaneous hypothalamic-pituitary-adrenal axis homolog: regulation by ultraviolet radiation. Am J Physiol Endocrinol Metab., vol. 301, p. E484-E493, 2011.*
S. A. Amundon et al. "Differential Responses of Stress Genes to Low Dose-Rate γ Irradiation", *Molecular Cancer Research*, Apr. 2003, p. 445-452, vol. 1.
S. Paul et al. "Development of gene expression signatures for practical radiation biodosimetry", *International Journal of Radiation Oncology Biology Physics*, Jul. 15, 2008, p. 1236-1244, vol. 71, No. 4.
K. Taki et al. "Microarray Analysis of Differentially Expressed Genes in the Kidneys and Testes of Mice after Long-term Irradiation with Low-dose-rate γ-rays", *Journal of Radiation Research*, 2009, p. 241-252, vol. 50, No. 3.
Y. Uehara et al. "Gene Expression Profiles in Mouse Liver after Long-Term Low-Dose-Rate Irradiation with Gamma Rays", *Radiation Research*, 2010, p. 611-617, vol. 174.
K. Seong et al. "Genome-wide analysis of low-dose irradiated male *Drosophila melanogaster* with extended longevity", *Biogerontology*, 2011, p. 93-107, vol. 12.
K. Knops et al. "Gene Expression in Low- and High-Dose-Irradiated Human Peripheral Blood Lymphocytes: Possible Applications for Biodosimetry", *Radiation Research*, 2012, p. 304-312, vol. 178, No. 4.
L. Jaafar et al. "Long-Term Effects of Ionizing Radiation on Gene Expression in a Zebrafish Model", *PLOS ONE*, Jul. 2013, vol. 8, Issue 7.
I. Nosel et al. "Characterization of gene expression profiles at low and very low doses of ionizing radiation", *DNA Repair*, 2013, p. 508-517, vol. 12.
W. Sudprasert et al., "Effects of low-dose gamma radiation on DNA damage, chromosomal aberration and expression of repair genes in human blood cells", International Journal of Hygiene and Environmental Health, 2006, pp. 503-511, vol. 209, No. 6.

(Continued)

*Primary Examiner* — David C Thomas
(74) *Attorney, Agent, or Firm* — Rabin & Berdo, P.C.

(57) ABSTRACT

Disclosed is a detection method for DNA repair-related genes which respond to low-level radiation, which includes the steps of (1) breeding AKR/J mice, as a thymus cancer model, and normal ICR mice in a low-dose radiation environment; (2) collecting thymuses from the AKR/J thymus cancer mouse model and the normal ICR mice which have been bred at the step (1); (3) analyzing genes in the thymuses collected at the step (2); (4) detecting, among the genes analyzed at the step (3), a DNA repair-associated gene expressed commonly or differentially in the AKR/J thymus cancer mouse model and the normal ICR mice; and (5) amplifying the gene detected at the step (4) and measuring the expression level thereof.

6 Claims, 3 Drawing Sheets

Specification includes a Sequence Listing.

(56) References Cited

OTHER PUBLICATIONS

M. C. Joiner et al., "Low-dose hypersensitivity: current status and possible mechanisms", International Journal of Radiation Oncology Biology Physics, 2001, pp. 379-389, vol. 49, No. 2.
International Search Report of PCT/KR2014/011853 dated Jun. 16, 2015.
Hyun Jung Koo et al., "Effects of red ginseng on the regulation of cyclooxygenase-2 of spleen cells in whole-body gamma irradiated mice", Food and Chemical Toxicology, 2013, pp. 839-846, vol. 62.
European Office Action dated Nov. 30, 2018.
H.S. Kim, "Expression of common or species specific DNA damage-repair pathway related genes in thymus of low-dose-rate irradiated AKR/J and ICR mice", Radiotherapy & Oncology, Journal of the European Society for Radiotherapy and Oncology, Feb. 2014, vol. 110, Supplement 1.
Jin Jong Bong et al., "Differential expression of thymic DNA repair genes in low-dose-rate irradiated KKR/J mice", Journal of Veterinary Science, 2013, pp. 271-279, vol. 14, No. 3.
Dhillon VS et al., "Genetic polymorphisms of genes involved in DNA repair and metabolism influence micronucleus frequencies in human peripheral blood lymphocytes", Mutagenesis, Jan. 2011, pp. 33-42, vol. 26, No. 1.
Kuwamoto K. et al., Possible involvement of enhanced prostaglandin E2 production in the photosensitivity in xeroderma pigmentosum group A model mice, J. Invest Dermatol., Feb. 2000, pp. 241-246, vol. 114, No. 2.
Emil Schüler et al., "Effects of internal low-dose irradiation from $^{131}$I on gene expression in normal tissues in Balb/c mice", EJNMMI Research, 2011, pp. 1-14, vol. 1, No. 29.

\* cited by examiner

DETECTION METHOD FOR DNA REPAIR-RELATED GENES WHICH RESPOND TO LOW-LEVEL RADIATION

TECHNICAL FIELD

The present invention relates to a detection method for DNA repair-associated genes responsive to low-dose radiation, and more particularly, to a method comprising exposing AKR/J mice, as a thymus cancer model, and normal ICR mice to low-dose radiation, collecting thymuses from the mice, identifying DNA repair-associated genes that are expressed commonly or differentially in response to radiation exposure, and amplifying the genes to measure expression levels thereof.

BACKGROUND ART

A variety of strategies have been applied to identify specific genes which are sensitive to low-dose radiation (0.7 mGy/h), but gene expression at the protein level has not been confirmed. In contrast, the genes identified in the present invention are revealed by differences in gene expression at the RNA level as well as at the protein level. Also, no attempts have been made to compare the expression patterns of genes associated with DAN damage and repair between healthy mice and cancer-induced mice, both of which are subjected to low doses of radiation. Moreover, it has not previously been known that the genes identified in the present invention are responsive to low-dose radiation. Some conventional studies, as will be described below, have characterized gene expression profiles which are responsive to low doses of radiation.

i) A human myeloid leukemia cell line was irradiated to a dose between 2 and 50 cGy, and the induction of five genes, CDKN1A, GADD45A, MDM2, BTG2 and PHLDA3, was observed (Amundson et al, 2003).

ii) When human blood was irradiated at doses of 0.5, 2 and 8 Gy, radiation-sensitive genes, FDXR, CDKN1A, PHPT1, BBC3 and SESN1, were identified, which have the potential for use to assess the amount of radiation exposure in the event of a radiation accident (Paul and Amundson, 2008).

iii) After C57BL/6J mice were irradiated at a dose rate of 0.032 to 13 μGy/min for a period of 485 days, kidneys and testicles were collected and subjected to microarray analysis, which identified genes sensitive to low doses of radiation (Taki et al, 2009).

iv) After male C57BL/6J mice were irradiated to 8 Gy, 0.4 Gy or 0.02 Gy at a dose rate of 17-20 mGy/day or 0.86-1.0 mGy/day for a period of 401 to 485 days, livers were collected and assessed by microarray analysis and reverse transcription polymerase chain reaction (RT-PCR), resulting in the identification of genes sensitive to low-dose radiation (Uehara et al, 2010).

v) Microarray and quantitative polymerase chain reaction (qPCR) analysis revealed 39 genes sensitive to low-dose radiation in Drosophila melanogaster exposed to low-dose radiation (Seong et al, 2011).

vi) When human blood was irradiated to 0, 0.02, 0.1, 0.5, 1, 2 and 4 Gy, microarray analysis revealed a total of nine genes responding to low doses of radiation. Also, gene groups differentially expressed according to dose rates and post-irradiation times were selected so as to be used for bio-dosimetry assay (Knops et al, 2012).

vii) Zebra Danio embryos were irradiated with 0.1 or 1 Gy, and liver mRNA was used for microarray and quantitative PCR analysis, resulting in the identification of radiation-sensitive genes (Jaafar et al, 2013).

viii) Human blood was exposed to 5 to 500 mGy radiation and assessed by microarray analysis, thus identifying genes sensitive to low-dose radiation (Nosel et al, 2013).

DISCLOSURE

Technical Problem

The interpretation of the data obtained from cell lines is generally difficult to directly apply to humans or animals, and animal experiments, which have employed mainly mice, show low cancer incidence and have many limitations in interpreting mouse responses to low-dose radiation as human responses. In order to overcome these problems, the present inventors conducted intensive and thorough research into carcinogenesis induced by radiation employing AKR/J mice, as a thymus cancer model, and normal ICR mice, which have been commonly widely used for cancer studies, resulting in differences in radiation responses being observed between the tumor model and normal mice, the differential responses being analyzed by the following method, leading to the present invention.

1) The thymus cancer model AKR/J mice and the normal ICR mice were exposed to low-dose radiation (0.7 mGy/h), and gene profiles responsive to low-dose radiation are identified in thymuses. 2) Then, focusing on genes associated with DNA repair, the genes are analyzed for their functions.

It is therefore an object of the present invention to provide a method of detecting a DNA repair-associated gene which responds to low-dose radiation, comprising the steps of (1) breeding AKR/J mice, as a thymus cancer model, and normal ICR mice in a low-dose radiation environment; (2) collecting thymuses from the AKR/J thymus cancer mouse model and the normal ICR mice which have been bred at the step (1); (3) analyzing genes in the thymuses collected at the step (2); (4) detecting, among the genes analyzed at the step (3), a DNA repair-associated gene expressed commonly or differentially in the AKR/J thymus cancer mouse model and the normal ICR mice; and (5) amplifying the gene detected at the step (4) and measuring the expression level thereof.

Technical Solution

In order to accomplish the above objects, the present invention provides a method of detecting a DNA repair-associated gene which responds to low-dose radiation, comprising the steps of (1) breeding AKR/J mice, as a thymus cancer model, and normal ICR mice in a low-dose radiation environment; (2) collecting thymuses from the AKR/J thymus cancer mouse model and the normal ICR mice which have been bred at the step (1); (3) analyzing genes in the thymuses collected at the step (2); (4) detecting, among the genes analyzed at the step (3), a DNA repair-associated gene expressed commonly or differentially in the AKR/J thymus cancer mouse model and the normal ICR mice; and (5) amplifying the gene detected at the step (4) and measuring the expression level thereof.

At the step (1), the low-dose radiation is characterized by being delivered at a dose rate of 0.7 mGy/h.

At the step (1), the mice are characterized by being housed in a low-dose radiation environment of 0.7 mGy/h until the total cumulative dose reaches 1.7 Gy.

At the step (5), the DNA repair-associated gene is characterized by being amplified with a primer selected from among primers specific to Cyp11a1, Ptgs2, Rnd3, Plxncl and cyp2el genes.

At the step (5), the expression level is characterized by being measured by a Venn diagram, quantitative polymerase chain reaction, detection assay for a specific protein and a statistical SAS program.

Advantageous Effects

As described above, the present invention provides a method of detecting a DNA repair-associated gene which responds to low-dose radiation, comprising the steps of (1) breeding AKR/J mice, as a thymus cancer model, and normal ICR mice in a low-dose radiation environment; (2) collecting thymuses from the AKR/J thymus cancer mouse model and the normal ICR mice which have been bred at the step (1); (3) analyzing genes in the thymuses collected at the step (2); (4) detecting, among the genes analyzed at the step (3), a DNA repair-associated gene expressed commonly or differentially in the AKR/J thymus cancer mouse model and the normal ICR mice; and (5) amplifying the gene detected at the step (4) and measuring the expression level thereof. Thereby, the present invention has the following effects: the genes have the potential for use as genetic markers for DNA repair in response to low-dose radiation, making it possible to evaluate the relationship between radiation exposure and carcinogenesis for industrial and medical workers; the genes can be applied as indicators for DNA repair in response to low-dose radiation for evaluating cancer progress and the effects of radiation therapy for cancer patients; and the genes can be applied to assess the dose-response relationship between radiation doses and cancer incidence.

BEST MODE

Figure 1:
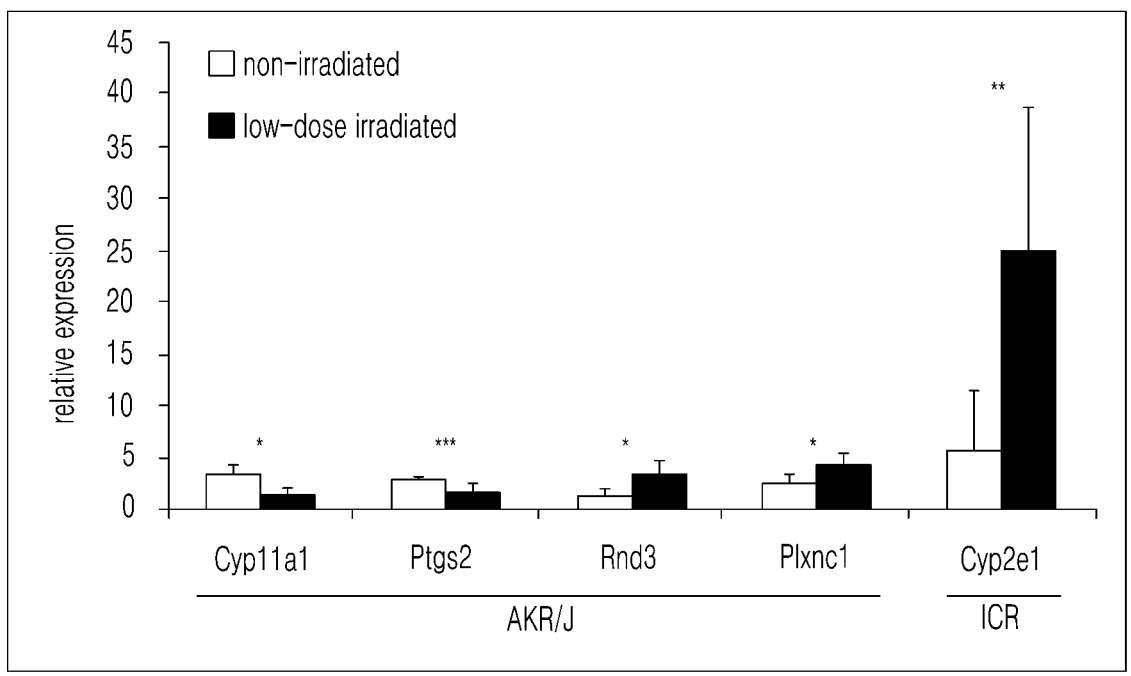
FIG. 1 is a graph showing the relative expression levels of genes, among genes associated with DNA damage and repair, being species-specifically responsive to low-dose radiation, the expression being analyzed by polymerase chain reaction.

Hereinafter, the present invention will be described in detail.

Generally, it is known that high-dose-rate radiation causes DNA damage and eventually induces cancer. In contrast, low-dose-rate radiation is known to stimulate repair of damaged DNA, apoptosis, immune responses and antioxidant capacity so that cancer incidence is suppressed. However, many cases do not satisfy the low dose rate ($\leq 6$ mGy/h) radiation recommended by the United Nations Scientific Committee on the Effects of Atomic Radiation (UNSCEAR 2000). Also, the interpretation of the data obtained from cell lines is generally difficult to directly apply to humans. Moreover, even if experimental animals were used, there are no conventional reports that confirm the effects of low-dose radiation on DNA repair with reference to protein levels. In the present invention, AKR/J mice and normal mice (ICR) were reared under low-dose-rate (0.7 mGy/h) irradiation. When mice started to die (Day 100), thymuses were collected and analyzed for gene expression. Also, from normal mice (ICR) reared under the same conditions, thymuses were collected and analyzed for gene expression. Finally, identified were DNA repair-associated genes expressed commonly or differentially between the two species of mice, and the genes were amplified for protein detection, thus affording genomic and proteomic profiling.

Mode for Invention

Hereinafter, the present invention will be explained in more detail with reference to the following examples. The following examples are provided only to illustrate the present invention, but it is to be understood that the present invention is not deemed to be limited thereto.

EXAMPLE 1

Seven-week-old female AKR/J mice and ICR mice were purchased from Shizuoka laboratory Center (Japan) and maintained under specific pathogen-free conditions for an adaptation period of one week. Five mice in each group were housed in a low-dose-rate (0.7 mGy/h) radiation facility for a period of 100 days until the total cumulative dose reached 1.7 Gy. Thereafter, thymuses were collected, rapidly frozen in liquid nitrogen, and analyzed for gene expression.

Gene expression patterns in the thymuses were compared between AKR/J mice and ICR mice, which were exposed to low-dose radiation. As a result, identified were DNA repair-associated genes responsive to low-dose-rate (0.7 mGy/h) radiation, and the genes were investigated for their functions.

The genes were analyzed using a Venn diagram, quantitative polymerase chain reaction, detection assay for specific proteins and the SAS statistical program (ANOVA, t-test).

For DNA repair-associated genes identified as radiation-responsive in thymuses from mice exposed to low-dose-rate (0.7 mGy/h) radiation, expression levels were analyzed using primers having nucleotide sequences listed in Table 1, below.

TABLE 1

| Gene accession No. | Genes | Forward (5'→3') | Reverse (5'→3') |
|---|---|---|---|
| NM_019779 | Cyp11a1 | CCTGGAAGAAAGACCG AATC (SEQ ID NO: 1) | TGCTTGATGCGTCTGTG TAA (SEQ ID NO: 2) |
| NM_011198 | Ptgs2 | AGAACCTGCAGTTTGC TGTG (SEQ ID NO: 3) | GCTCCTGCTTGAGTAT GTCG (SEQ ID NO: 4) |

TABLE 1-continued

| Gene accession No. | Genes | Forward (5'→3') | Reverse (5'→3') |
|---|---|---|---|
| NM_028810 | Rnd3 | TATGACAACGTCCGTCCACT (SEQ ID NO: 5) | CCTGGATTTCACCTTTCCAC (SEQ ID NO: 6) |
| NM_018797 | Plxnc1 | TCCTCATCCCATGAAGAACA (SEQ ID NO: 7) | CGCTGCTAAGCACTCTGAAC (SEQ ID NO: 8) |
| NM_021282 | Cyp2e1 | TCTCTTCAACAAACGCTTCG (SEQ ID NO: 9) | CCAGGGAGTACTCAGCAGGT (SEQ ID NO: 10) |

TEST EXAMPLE 1

Measurement of Expression Levels of DNA Damage/Repair-Associated Genes

After AKR/J mice and ICR mice were exposed to low-dose-rate (0.7 mGy/h) radiation, thymuses were collected at the early stage of carcinogenesis (Day 100). Focusing on genes associated with DNA damage and repair, genes species-specifically responsive to low-dose radiation were selected and analyzed for relative expression levels via polymerase chain reaction.

As shown in FIG. 1, Cyp11a1, Ptgs2, Rnd3 and Plxnc1 genes in AKR/J mice irradiated with low-dose radiation and cyp2e1 gene in ICR mice were found to be species-specifically responsive to low-dose radiation.

TEST EXAMPLE 2

Evaluation for Protein Expression in Thymuses from Low-Dose Radiation-Irradiated AKR/J and ICR Mice Protein expression levels were estimated in the mouse thymuses prepared in Example 1, which were irradiated with low-dose radiation, along with a control group in which mice were exposed to high-dose radiation (0.8 Gy/min, the total dose: 4.5 Gy).

Figure 2:
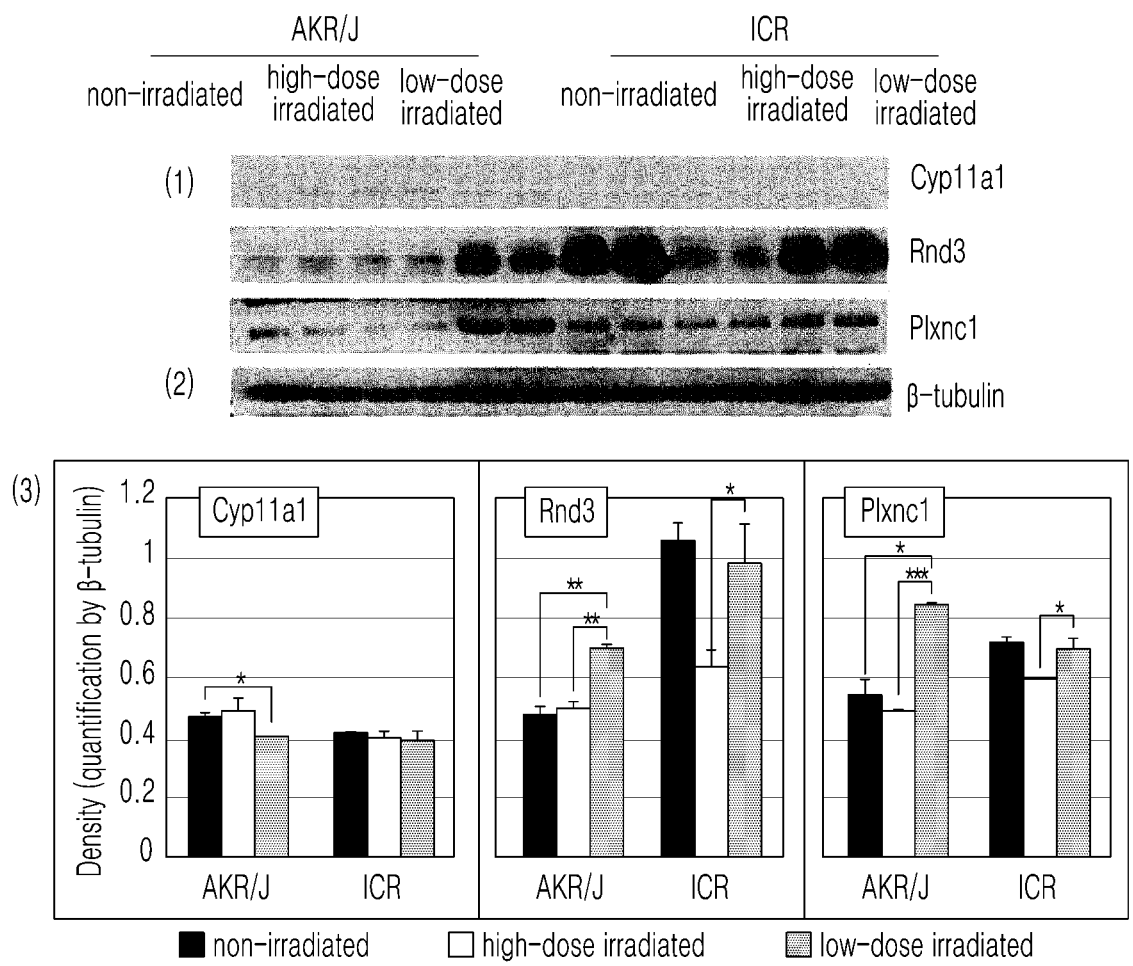
FIG. 2 shows the protein expression levels in thymuses from AKR/J mice and ICR mice, both of which were exposed to low-dose radiation ((1) DNA repair-associated genes in response to low-dose radiation (Cyp11a1, Rnd3 and Plxncl), (2) loading control, and (3) quantitative analysis for proteins of interest, in which the density of each protein band was measured and quantified relative to the density of β-tubulin)
Figure 3:
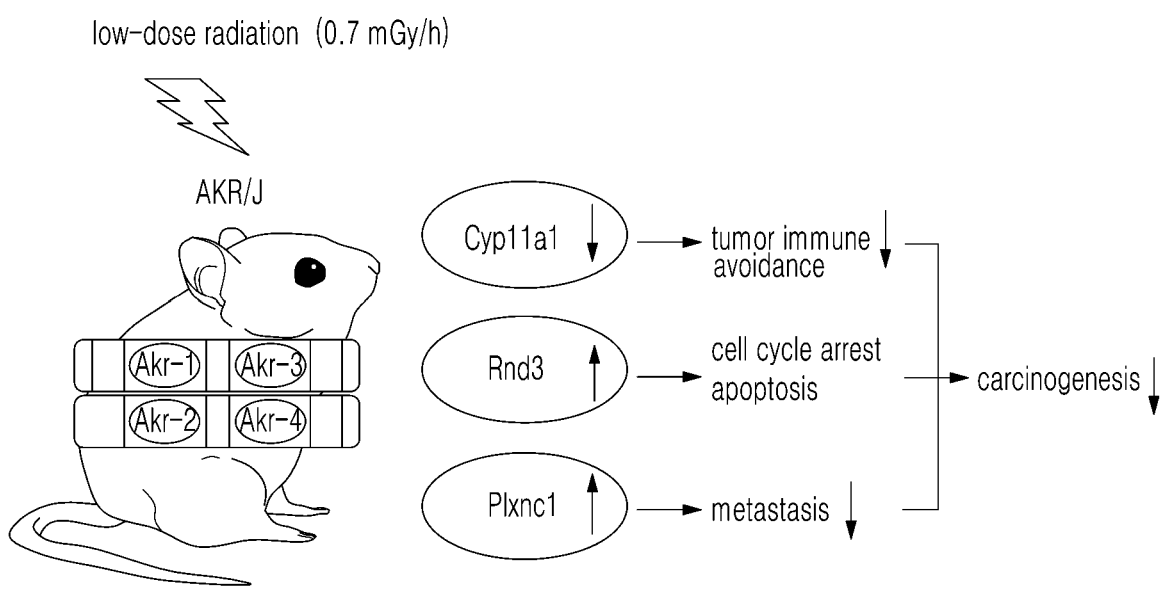
FIG. 3 is a schematic diagram showing gene expression responses to low-dose radiation and subsequent cellular changes in the thymus from a mouse exposed to low-dose radiation.

As shown in FIG. 2, in the AKR/J mice irradiated with low-dose radiation, Cyp11a1, Rnd3 and Plxnc1 genes were identified as species-specifically responsive to low-dose radiation.

Hereinbefore, the present invention has been described in detail with reference to specific examples thereof. Although the preferred embodiments of the present invention have been disclosed for illustrative purposes, those skilled in the art will appreciate that various modifications, additions and substitutions are possible, without departing from the scope and spirit of the invention. Thus, the actual scope of the present invention will be defined by the appended claims and equivalents thereof.

<Sequence Listing Free Text>

The sequence listing was submitted as an electronic file.

What is claimed is:

1. A method of detecting a DNA repair-associated gene which responds to low-dose radiation, comprising the steps of:
   (1) breeding a thymus cancer mouse model and a normal mouse in a low-dose radiation environment, wherein the thymus cancer mouse model and the normal mouse are housed in a low-dose radiation environment of 0.7 mGy/h until a total cumulative dose reaches 1.7 Gy (gray);
   (2) collecting thymuses from the thymus cancer mouse model and the normal mouse which have been bred at the step (1);
   (3) analyzing genes in the thymuses collected at the step (2);
   (4) detecting, among the genes analyzed at the step (3), a DNA repair-associated gene expressed commonly or differentially in the thymus cancer mouse model and the normal mouse, wherein the DNA repair-associated gene is Ptgs2 (prostaglandin-endoperoxide synthase 2) gene; and
   (5) amplifying the gene detected at the step (4) and measuring an expression level thereof.

2. The method of claim 1, wherein, at the step (5), the expression level is measured by a Venn diagram, quantitative polymerase chain reaction, detection assay for a specific protein and a SAS statistical program.

3. A method of detecting a DNA repair-associated gene which responds to low-dose radiation, comprising the steps of:
   (1) breeding a thymus cancer mouse model and a normal mouse in a low-dose radiation environment, wherein the thymus cancer mouse model and the normal mouse are housed in a low-dose radiation environment of 0.7 mGy/h until a total cumulative dose reaches 1.7 Gy (gray);
   (2) collecting thymuses from the thymus cancer mouse model and the normal mouse which have been bred at the step (1);
   (3) analyzing genes in the thymuses collected at the step (2);
   (4) detecting, among the genes analyzed at the step (3), a DNA repair-associated gene expressed commonly or differentially in the thymus cancer mouse model and the normal mouse, wherein the DNA repair-associated gene is Rnd3 (Rho family GTPase 3) gene; and
   (5) amplifying the gene detected at the step (4) and measuring an expression level thereof.

4. The method of claim 3, wherein, at the step (5), the expression level is measured by a Venn diagram, quantitative polymerase chain reaction, detection assay for a specific protein and a SAS statistical program.

5. A method of detecting a DNA repair-associated gene which responds to low-dose radiation, comprising the steps of:
   (1) breeding a thymus cancer mouse model and a normal mouse in a low-dose radiation environment, wherein the thymus cancer mouse model and the normal mouse are housed in a low-dose radiation environment of 0.7 mGy/h until a total cumulative dose reaches 1.7 Gy (gray);
   (2) collecting thymuses from the thymus cancer mouse model and the normal mouse which have been bred at the step (1);
   (3) analyzing genes in the thymuses collected at the step (2);
   (4) detecting, among the genes analyzed at the step (3), a DNA repair-associated gene expressed commonly or differentially in the thymus cancer mouse model and the normal mouse, wherein the DNA repair-associated gene is Plxnc1 (plexin C1) gene; and
   (5) amplifying the gene detected at the step (4) and measuring an expression level thereof.

6. The method of claim 5, wherein, at the step (5), the expression level is measured by a Venn diagram, quantitative polymerase chain reaction, detection assay for a specific protein and a SAS statistical program.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Forward primer to Cyp11a1

<400> SEQUENCE: 1
cctggaagaa agaccgaatc                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse primer to Cyp11a1

<400> SEQUENCE: 2
tgcttgatgc gtctgtgtaa                                              20

<210> SEQ ID NO 3
<211> LENGTH: 20
<212> TYPE: DNA
<213> ORGANISM: Artificial Sequence
```

```
<220> FEATURE:
<223> OTHER INFORMATION: Forward primer to Ptgs2

<400> SEQUENCE: 3
agaacctgca gtttgctgtg                                              20

<210> SEQ ID NO 4
<211> LENGTH: 20
<212> TYPE: DNA
<213> ORGANISM: Artificial Sequence
<220> FEATURE:
<223> OTHER INFORMATION: Reverse primer to Ptgs2

<400> SEQUENCE: 4
gctcctgctt gagtatgtcg                                              20

<210> SEQ ID NO 5
<211> LENGTH: 20
<212> TYPE: DNA
<213> ORGANISM: Artificial Sequence
<220> FEATURE:
<223> OTHER INFORMATION: Forward primer to Rnd3

<400> SEQUENCE: 5
tatgacaacg tccgtccact                                              20

<210> SEQ ID NO 6
<211> LENGTH: 20
<212> TYPE: DNA
<213> ORGANISM: Artificial Sequence
<220> FEATURE:
<223> OTHER INFORMATION: Reverse primer to Rnd3

<400> SEQUENCE: 6
cctggatttc acctttccac                                              20

<210> SEQ ID NO 7
<211> LENGTH: 20
<212> TYPE: DNA
<213> ORGANISM: Artificial Sequence
<220> FEATURE:
<223> OTHER INFORMATION: Forward primer to Plxnc1

<400> SEQUENCE: 7
tcctcatccc atgaagaaca                                              20

<210> SEQ ID NO 8
<211> LENGTH: 20
<212> TYPE: DNA
<213> ORGANISM: Artificial Sequence
<220> FEATURE:
<223> OTHER INFORMATION: Reverse primer to Plxnc1

<400> SEQUENCE: 8
cgctgctaag cactctgaac                                              20

<210> SEQ ID NO 9
<211> LENGTH: 20
<212> TYPE: DNA
<213> ORGANISM: Artificial Sequence
<220> FEATURE:
<223> OTHER INFORMATION: Forward primer to cyp2el

<400> SEQUENCE: 9
tctcttcaac aaacgcttcg                                              20
```

```
<210> SEQ ID NO 10
<211> LENGTH: 20
<212> TYPE: DNA
<213> ORGANISM: Artificial Sequence
<220> FEATURE:
<223> OTHER INFORMATION: Reverse primer to cyp2el

<400> SEQUENCE: 10
ccagggagta ctcagcaggt                                               20
```